United States Patent

Rees

[11] Patent Number: 5,776,153
[45] Date of Patent: Jul. 7, 1998

[54] ANGIOPLASTY CATHETER WITH GUIDEWIRE

[75] Inventor: Michael Ralph Rees, Avon, Great Britain

[73] Assignee: Medical Miracles Company Limited, United Kingdom

[21] Appl. No.: 581,551

[22] PCT Filed: Jul. 4, 1994

[86] PCT No.: PCT/GB94/01446

§ 371 Date: Apr. 3, 1996

§ 102(e) Date: Apr. 3, 1996

[87] PCT Pub. No.: WO95/01752

PCT Pub. Date: Jan. 19, 1995

[30] Foreign Application Priority Data

Jul. 3, 1993 [GB] United Kingdom .................. 9313810
Nov. 13, 1993 [GB] United Kingdom .................. 9323474

[51] Int. Cl.$^6$ ............................................. A61B 17/22
[52] U.S. Cl. .................................................. 606/159
[58] Field of Search ........................... 606/159, 170, 606/171, 180

[56] References Cited

U.S. PATENT DOCUMENTS

| 4,646,736 | 3/1987 | Auth | 606/159 |
|---|---|---|---|
| 4,854,325 | 8/1989 | Stevens | 606/159 |
| 4,936,845 | 6/1990 | Stevens. | |
| 5,116,350 | 5/1992 | Stevens. | |
| 5,127,917 | 7/1992 | Niederhauser et al.. | |
| 5,243,997 | 9/1993 | Uflacker et al.. | |
| 5,443,078 | 8/1995 | Uflacker. | |

FOREIGN PATENT DOCUMENTS

| 89310637 | 10/1989 | European Pat. Off.. |
|---|---|---|
| 0 401 158 A1 | 5/1990 | European Pat. Off.. |
| 3327855A1 | 7/1983 | Germany. |
| 91 10 902.7 | 3/1992 | Germany. |
| WO92/08510 | 5/1992 | WIPO. |

*Primary Examiner*—Michael Buiz
*Assistant Examiner*—Kevin Truong
*Attorney, Agent, or Firm*—Gifford, Krass, Groh, Sprinkle, Patmore, Anderson & Citkowski, P.C.

[57] ABSTRACT

Angioplasty apparatus comprises a hand-held unit which reciprocates a wire within a catheter. It is found that, by using a highly flexible wire and a reciprocation frequency of 50–1000 Hz a diffuse vibration is caused at the distal end of the wire which enables the wire to pass relatively easily through difficult blockages.

9 Claims, 6 Drawing Sheets

ANGIOPLASTY CATHETER WITH GUIDEWIRE

This invention relates to a novel apparatus for use in angioplasty, and to a method of carrying out angioplasty.

Angioplasty is a technique for treating constriction of a blood vessel or heart valve by introducing a balloon into the constriction to widen it. A blood vessel may be a coronary vessel or a peripheral vessel. A hollow needle is generally inserted into the femoral artery. A guide wire is pushed through the needle into the artery, then along it, with the aid of imaging equipment, towards the blood vessel or heart valve to be treated. If there is a stenosis (narrowing) through which the guide wire can pass, it is advanced through it. A catheter is then threaded over the guide wire and pushed along it until it reaches the constriction. The catheter has an end region which can be inflated to form a balloon. The balloon is inflated and deflated, generally a few times, to widen the constriction, and then withdrawn. Sometimes the catheter is already engaged on the wire as the wire is advanced, the distal end of the wire extending beyond the distal end of the catheter.

There is a wide variety of balloon technology available. Balloons of various sizes from 1.5 mm to 30 mm in diameter may be obtained.

A problem arises when a blood vessel or heart valve is so occluded that the guide wire cannot simply be passed through the occlusion. A plethora of techniques has been proposed to overcome this problem. Work has been done on laser systems, but it has proved difficult to find a system which will ablate an occlusion without causing damage to the surrounding tissue. Thermal damage from continuous wave lasers can be very extensive whilst pulse lasers may have a smaller effect on surrounding tissues, but often fail to deliver sufficient energy over a large enough region to effect ablation. Mechanical devices have also been proposed. For example, the Kensey catheter employs a blunt rapidly rotating cam together with a fluid jet which creates a vortex at the tip of the catheter. The occlusion is pulverised by a combination of mechanical energy and the action of the fluid jet forming small particles which are dissipated into the blood stream. However, a high number of perforations and dissections in severely diseased vessels, where the arterial wall is calcified and therefore less compliant, have been observed. A lower speed rotational device known as the Rotacs system has also been used. Such a device is not designed to ablate an occlusion, but to provide some mechanical energy to the wire, to enable it to find the path of least resistance through an occluded vessel. However, the success rate with such a device is not very high.

A further idea has been to use hydrophilic guide wires, introduced by standard manual procedures. These are proprietary wires, thought to be of tantalum or stainless steel, coated with a proprietary material to make them slippery. This is thought to help them to take the path of least resistance through an occlusion. These wires are simple to use but a significant disadvantage is that there is a tendency to effect a sub-intimal passage of the wire past the occlusion. That is to say, the wire , tends to find a route through the wall of a vessel, rather than through the central region of an occlusion.

Despite the substantial earlier body of work aiming to devise a system to improve angioplasty as applied to occluded vessels and valves, no prior system has been wholly satisfactory.

In accordance with the present invention there is provided apparatus for use in angioplasty, comprising a catheter, a wire which serves as a guide for the catheter and whose distal end extends, in use, beyond the distal end of the catheter, and a drive unit which is coupled to the proximal end of the wire so as to vibrate the proximal end.

Preferably the catheter comprises means to act upon a blood vessel to improve or restore its function. Thus, it may comprise an expandable balloon at its distal end, although other forms of catheter may be used.

In use, the wire is fed through blood vessels to an occlusion. The catheter may then be introduced into the body, by being passed along the wire. Alternatively, and preferably, the catheter may have already been located on the wire as the wire was fed up to the occlusion, or may have been pushed in without the wire. In the region of the occlusion, once the apparatus is to be used to vibrate the wire, the distal end of the wire extends beyond the distal end of the catheter. The drive unit is then operated to vibrate the proximal end of the wire. The vibration passes along the wire and, at the distal end of the wire, this vibration is thought to be diffuse in nature; even if, as is preferred, the vibration imparted to the wire at the proximal end is predominantly or wholly a reciprocating motion. In any event, whatever the nature of the vibration of the distal end of the wire, it has been found, in preliminary confidential trials, that the wire readily finds or forms a central passage through the occlusion. It appears that the vibrating wire may alter the characteristics of the plaque which makes up the occlusion. Furthermore the vibration of the wire and/or the consequent vibration of the catheter, appears to relax the blood vessel. Once the wire has passed through the occlusion, it is found that the catheter can be advanced, so that the balloon is within the occlusion, more easily than has heretofore been found. It is then found that the occlusion may be widened by much lower balloon pressures than has previously been the case.

In the method of using the apparatus, the drive unit is generally only operated until the wire has passed through the occlusion. Nevertheless the further advantages, of easier subsequent catheter advancement, and easier widening of the occlusion, are, most surprisingly, still found. As yet we have no theory to explain why this should be so.

Preferably, the drive unit vibrates, preferably reciprocates, the proximal end of the wire at a frequency in the range 30–1,000 Hz. Preferably it can vibrate, preferably reciprocate, the wire at a frequency in the range 50–1000 Hz, more preferably 50–500 Hz. Preferably sub-ranges may be 100–500 Hz, and, for cardiac work, 200–400 Hz. Preferably, the drive unit is adjustable, to vibrate, preferably reciprocate, the proximal end of the wire at a frequency to be selected.

Preferably the vibration applied to the wire is a reciprocation, and the drive unit reciprocates the proximal end of the wire by a stroke in the range 0.1–5 mm, for example 1–5 mm, preferably 2–4 mm, or 0.1–1 mm, preferably 0.2–0.5 mm. This too may be adjustable.

The drive unit may comprise electric motor, or an air driven motor, or a solenoid.

Preferably the apparatus comprises means for adjustably clamping the wire, preferably comprising spring loaded quick release means.

The apparatus may comprise means for adjusting the force with which the wire is accelerated. To this end the wire may be spring loaded and the spring force may be varied. In one embodiment the drive unit operates to draw back the wire, against the spring force. The wire is then released to be driven forward by the spring force. In another embodiment the drive unit drives the wire forward and the spring force urges the wire backward.

The apparatus may comprise means for vibrating, preferably reciprocating, the catheter. Such means may be similar means to those described above with reference to the wire. In use the catheter may thus be vibrated, preferably reciprocated, in order to facilitate its passage through an occlusion that has already been passed by a wire. Whilst the catheter is thus vibrated the wire may be fixed. In other embodiments the wire may still be vibrated, the wire and the catheter thus being simultaneously vibrated, either by the same mechanism, or by different mechanisms, whereby the vibration/reciprocation characteristics—stroke, frequency, force etc—may be different, for the wire and the catheter.

Preferably, the apparatus has means for clamping the catheter. Suitably the apparatus comprises means for non-adjustably clamping the catheter. The catheter may have a collar at its proximal end and the apparatus may then have quick release means for clamping the collar.

The two clamping means may be adjustably spaced apart in some embodiments.

Preferably the apparatus comprises a housing carrying the said clamping means, and containing the drive unit, and any control means whereby adjustment of the operating conditions, as described above, may be effected. The housing may be suitable for hand-held use. Preferably, the housing is pistol-shaped, the wire and catheter being axially aligned with respect to the barrel. Suitably the means for clamping the catheter is located at the free end of the barrel. Suitably the apparatus is such that the wire can extend right through the barrel and be fed into a patient by progressively advancing it through the barrel, until it reaches the occlusion. It can then be clamped and vibrated, preferably reciprocated, and its advance is accompanied by an advance of the entire apparatus. The barrel may be removable to allow for cleaning and interchangeable to allow for different catheters to be fitted to the apparatus. There may be provided a kit comprising a butt portion housing the drive unit and a plurality of alternate barrels securable thereto, adapted to take different catheters.

Preferably, the wire is at least one metre in length, measured from the drive unit. The characteristics of the wire are thought to be important. It is not desired to employ a wire which produces a ramming motion at its distal end. Rather, it is desired to employ a wire which can produce a diffuse movement in three dimensions at its distal end. Preferably at least the distal end region of the wire end region of the wire is "floppy".

If one considers a catheter and wire held horizontally, with the distal end region projecting from the catheter, we would consider the distal end region to be "floppy", and suitable for use in the present invention, if it was unable to stay straight under its own weight, but rather bowed or drooped downwards, when it projected 10 cm or less beyond the end of the catheter. A particularly preferred "floppy" wire would have a distal end which bowed or drooped downwards when thus projected 5 cm or less, preferably 3 cm or less, beyond the end of the catheter.

The distal end region of a wire may be suitably "floppy" because of the type of material selected and/or because of the thin gauge of wire selected, and/or because of the construction of the wire. One suitable type of wire is a normal cylindrical angioplasty wire of thin gauge. Such a wire may have, at least at its distal end, but preferably throughout, a diameter in the range 0.11 mm, preferably 0.2–12 mm (preferably 0.25–0.9 mm, most preferably 0.25–0.6 mm, for coronary and tibial arterial procedures; and preferably 0.6–0.9 mm for other arterial procedures).

Another suitable wire has a distal end region which is of coiled construction. Unlike some wires intended for a ramming motion the coiled end region does not surround a core wire, which would make the distal end region rigid.

Preferably, the distal tip of the wire is smooth. It may be bulbous, and if so preferably has a diameter, or mean diameter, measured in the transverse direction, in the range 0.5–1.5 mm, most preferably 0.8–1.2 mm. It may be spherical but most preferably it is of ovoid or olive-shaped. Alternatively it may be of simple rounded-off form.

It is preferred that the wire, at least at its distal end region but preferably throughout, is a low-friction "slippy" wire. Such wire will be familiar to those skilled in the art. A suitable low-friction wire may have a microscopically smooth surface achieved by polishing, or may be coated with a low-friction material. Some such coatings are known as hydrophilic coatings.

Preferably, the bore or lumen of the catheter is slightly oversized, relative to the wire. Preferably the diameter of the lumen or bore is larger than the diameter of the wire by about 10–50%, preferably by about 20–40%.

The invention extends to a kit of parts for assembling an apparatus as defined above, such assembly generally being effected immediately prior to, or during, a procedure, and to a method of using apparatus as defined above, the method also being as described herein. The method may be used in angioplasty for any occluded vessel, but preferably is used in coronary angioplasty.

In accordance with a further, independent, aspect of the present invention there is provided apparatus for use in angioplasty, comprising a pistol-shaped unit, preferably suitable to be held in the hand, which is coupled, in use, to elongate means introduced into blood vessels of a patient during angioplasty.

The invention will now be further described, by reference to the accompanying drawings, which show, in schematic form, by way of example only, two embodiments of the present invention, as follows.

Figure 2:
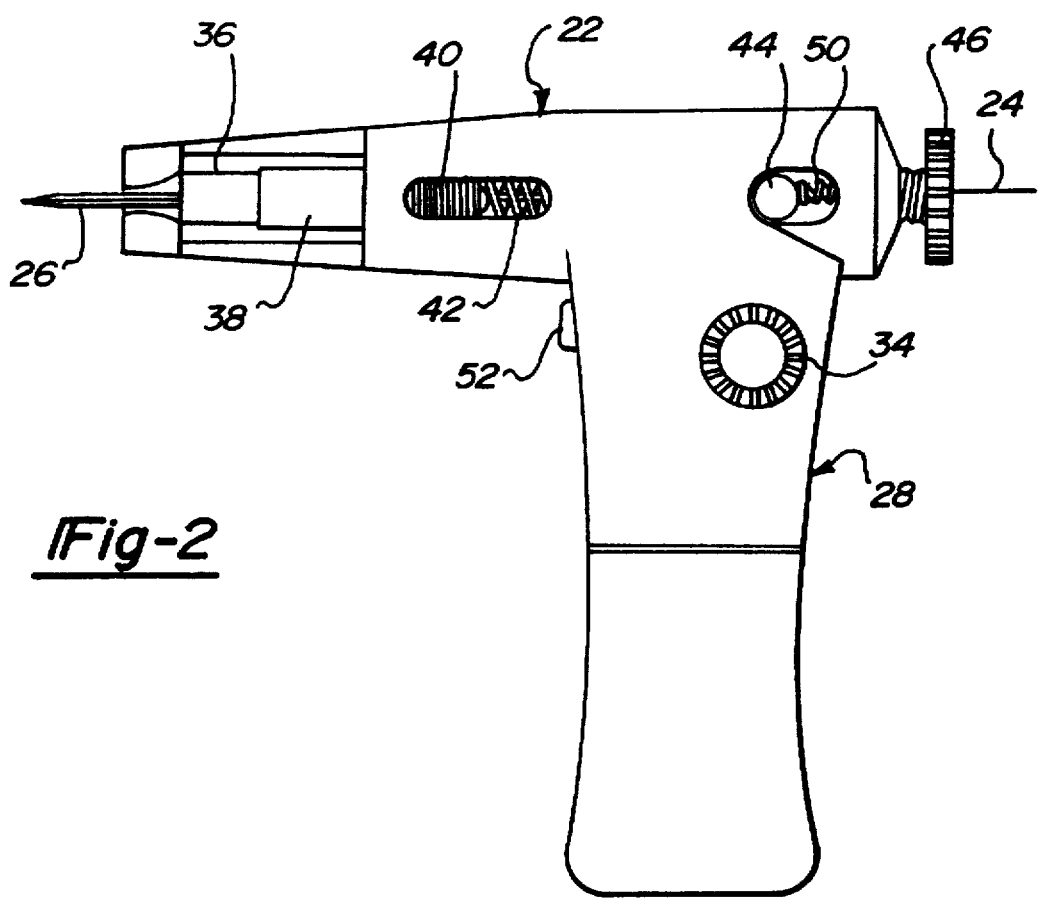
FIG. 2 is a side elevation of a second embodiment.
Figure 3:
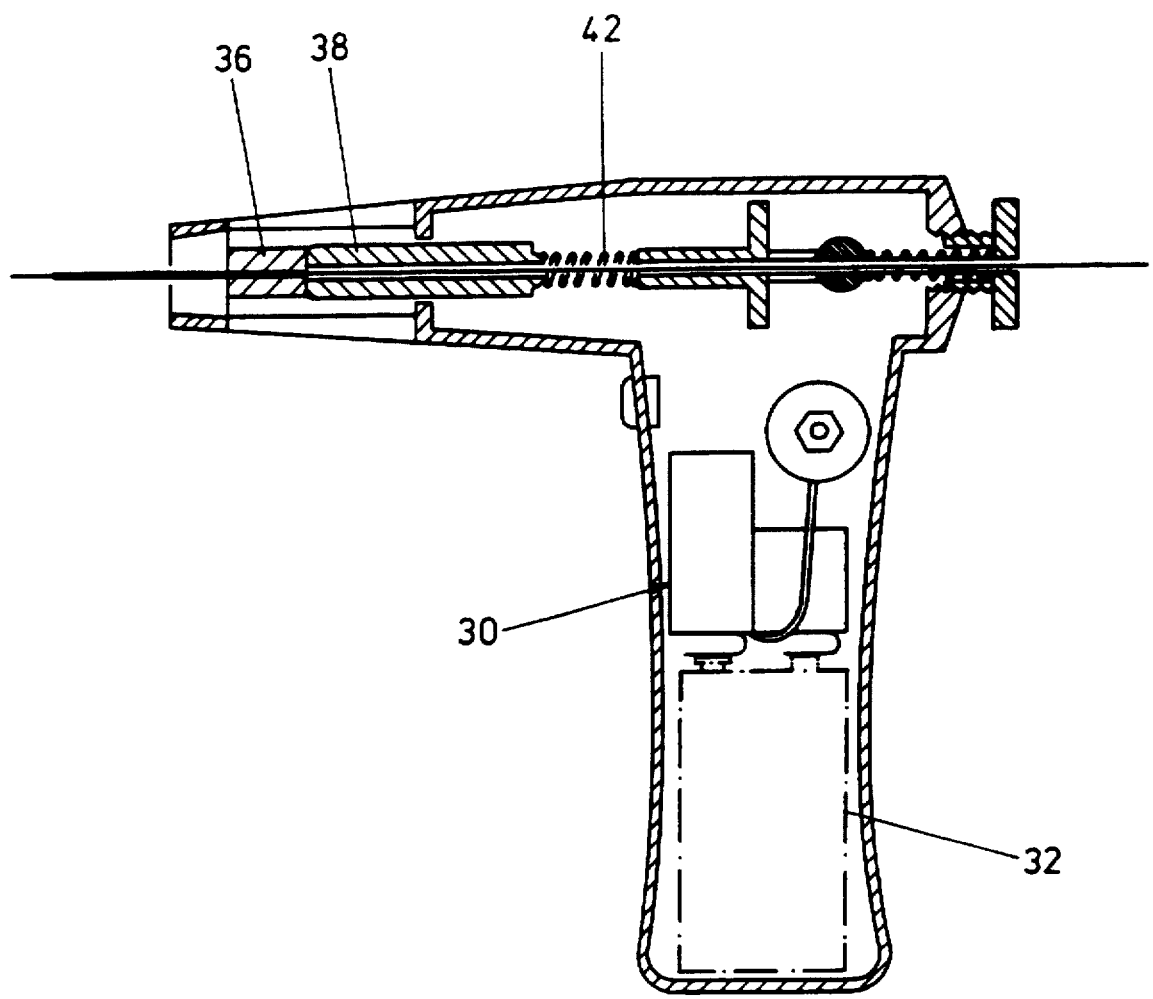
FIG. 3 is a cross-section view thereof.
Figure 4:
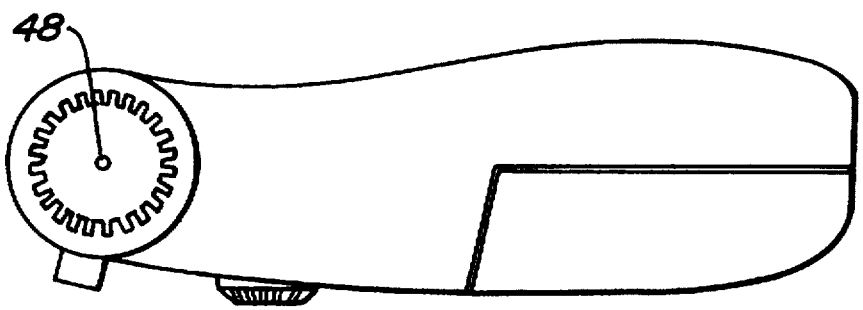
FIG. 4 is an elevation from the butt end.
Figure 5:
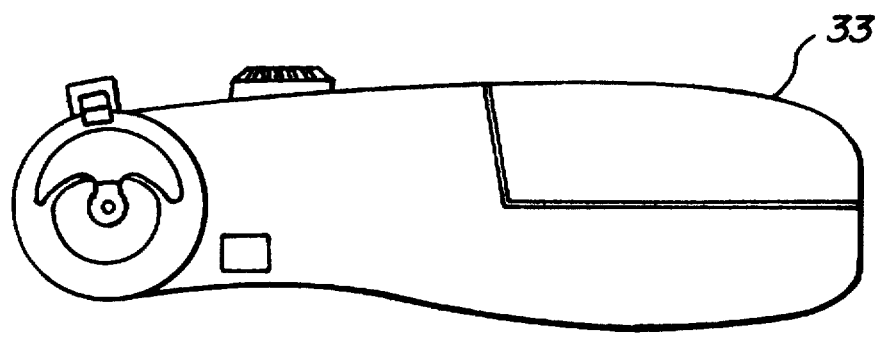
FIG. 5 is an end elevation from the opposite end to FIG. 4.
Figure 6:
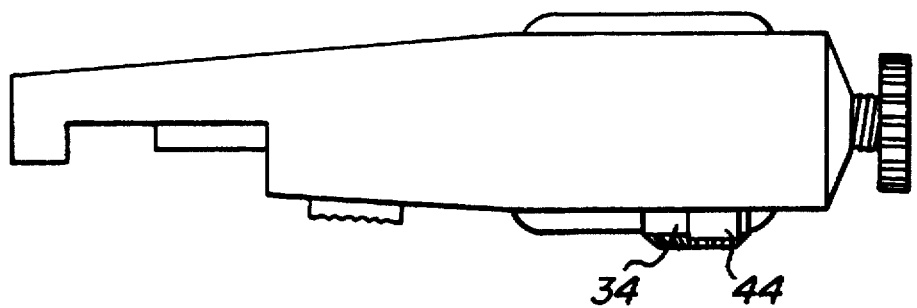
FIG. 6 is a view from above.
Figure 7:
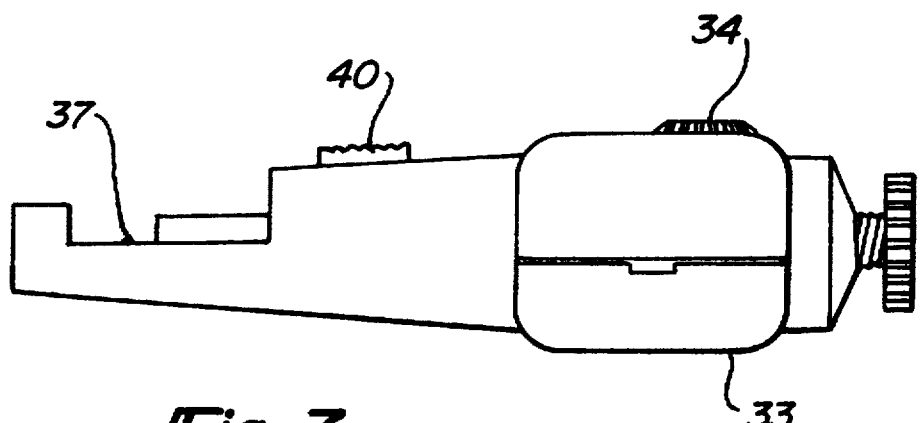
FIG. 7 is a view from below.
Figure 8:
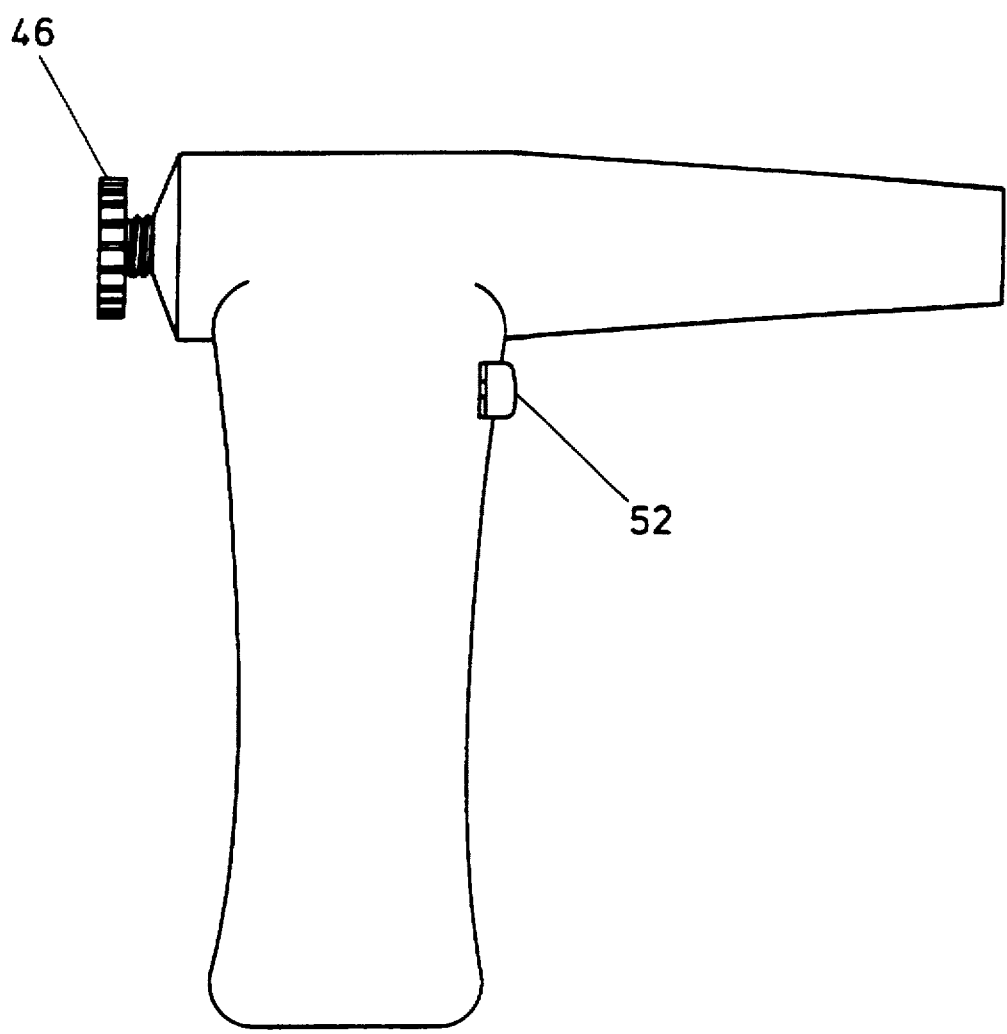
FIG. 8 is a side elevation, showing the opposite side to that shown in FIG. 4.

In the drawings of the second embodiment, FIGS. 2 and 3 show a catheter and wire in place, whilst FIGS. 4 to 8 do not.

Figure 1:
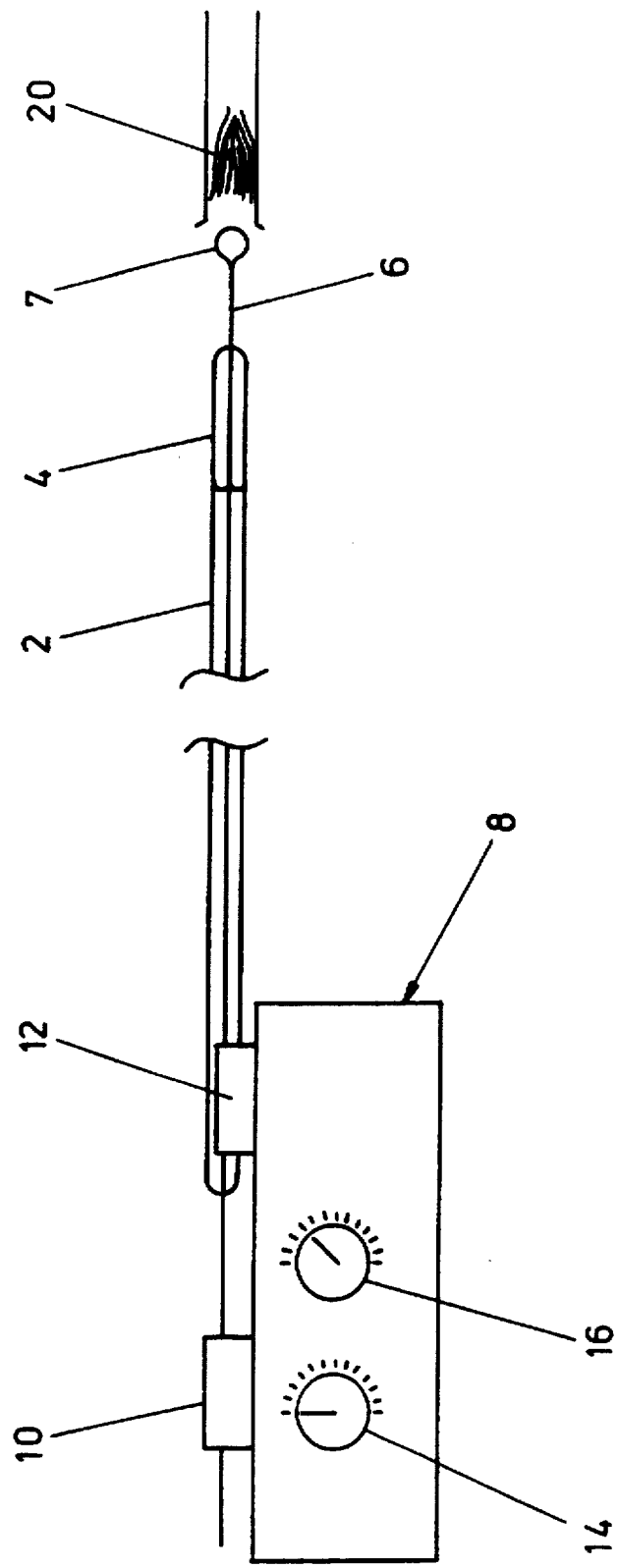
FIG. 1 is a first embodiment.

As shown in FIG. 1, angioplasty apparatus comprises, as is conventional, a balloon catheter 2, having an annular expandable balloon chamber 4 at its distal end; and a narrow-gauge, "floppy" wire 6, passing through the catheter, such that its distal end extends beyond the catheter. The tip 7 of the wire is olive-shaped in this particular embodiment.

At their proximal ends the catheter and wire are connected to a drive unit 8. The drive unit 8 has a housing within which is located an electric or air motor and a drive train to impart reciprocating motion to a clamping block 10 within which the proximal end of the wire is releasably clamped. In front of the block 10, and in alignment with it, is a clamping block 12 which releasably clamps the catheter 2.

The details of the motor and drive train need not be discussed here as these are well within the compass of the person skilled in the art. It is sufficient to state that the reciprocating stroke of the block 10 is adjustable, as is the frequency of reciprocation. These are respectively adjusted by dials 14, 16.

The housing for the drive unit 8 is small enough to be held in the hand.

The clamping block 12 of the catheter is adjustably mounted on a track (not shown) so that the spacing between the blocks 10 and 12 is adjustable, between about 10 and 40 mm (measured between the clamping positions).

In this embodiment, the diameter of the wire 6 is about 0.4–0.45 mm, and the transverse diameter of the olive-shaped tip is about 1 mm. The wire bows under its own weight when projected about 3 cm or more beyond the end of the catheter. At a projected length of 5 cm the tip of the wire droops down by at least 1 cm, with the rest of the wire and the catheter held horizontally. The diameter of the catheter is about 1 mm and the balloon is expandable to a diameter of about 3 mm. The frequency with which the guide wire can be reciprocated by the drive unit may be adjusted to any frequency between 50 and 500 Hz. 200–300 Hz is thought to be most effective for most conditions, but lower frequencies, such as 60 and 120 Hz have been known to be effective, provided a sufficiently "floppy" wire is used. The diameter of the bore of the catheter is about 0.6–0.65 mm. The reciprocation stroke of the wire is adjustable between 0.1 and 5 mm. 0.2–2 mm is thought to be most effective, for most conditions, with this embodiment.

The clamps associated with the blocks 10, 12 may be of any form. Conveniently the clamp for the wire may be a diaphragm clamp, the diaphragm being pressed down on to the wire by a screw. This is known as the Tuoey-borst system. The block 12 may comprise a slot to receive the catheter, and an adjustable strap extending over the catheter and the block. By means of such clamps a single apparatus is suitable for procedures which may involve a wide range of wire and catheter sizes.

In an angioplasty procedure, the guide wire is introduced into the body via the femoral artery and is guided into place up to the occlusion shown as 20. If the catheter has not already been located on the guide wire, it is now fed along it until its end is close to the tip of the guide wire—generally between 10 and 30 cm from it. The guide wire and catheter are then clamped in place. The unit is then switched on and the frequency and reciprocation stroke adjusted as required. As the guide wire advances through the occlusion the drive unit can be advanced but preliminary observations indicate that it may be better to position the drive unit in a fixed location and to progressively advance the guide wire, by successively releasing and re-clamping it, whilst leaving the catheter clamped in the same position throughout.

Preliminary trials have indicated that the wire advances easily through the occlusion and no propensity for it to deviate from vessel, or pass along the wall of the vessel, has been observed. It has been found to substantially ease the subsequent advancement of the catheter so that the balloon is located within the occlusion. Moreover, most surprisingly, it has been found that the required expansion of the balloon 4 can be effected at very much lower pressures than has previously been the case. For example, in a procedure which would have normally required an expansion pressure of about 12 atmospheres, an expansion pressure of 2–3 atmospheres has been employed, using the method and apparatus of the invention.

In the second embodiment the apparatus is pistol-shaped, and sized to fit in the hand of the operative, typically a cardiologist.

The apparatus comprises a barrel 22 having an axis with which the wire 24 and catheter 26 are aligned. It also comprises a butt portion 28 within which is located a drive unit 30 and battery power supply 32, accessible by means of a removable wall portion 33. Externally the butt portion carries a dial 34 by means of which the frequency of reciprocation is controlled.

The catheter terminates, at its proximal end, in a collar 36, and this collar is clamped within a recess 37 at the free end of the barrel 22. It is clamped therein by retracting a clamping block 38, controlled by an externally projecting, ridged moulding 40, and is spring loaded by means of spring 42 located within the barrel.

The wire is clamped within the barrel under the control of an externally projecting clamping knob 44, arranged transversely to the barrel 22. Beneath the clamping knob, not shown, is a helical spring. Pushing the clamping knob, against the spring force, moves an aperture into alignment with a second aperture for the wire, so that the wire can be freely fed through both apertures. Releasing the clamping knob moves those apertures out of alignment, so that the wire is clamped therebetween. When the drive unit is operated, the knob 44 is reciprocated, and thus the wire is reciprocated.

At the butt end of the barrel a reciprocation control knob 46 is located, being adjustably screw threaded within a threaded bore at the butt end. The control knob 46 has a central aperture 48 through which the wire 24 may freely move. Retained in compression between the control knob and the clamping knob 44 is a helical spring 50. The position of the control knob 46 controls the compression of the spring 50. The drive unit operates to pull back the clamping knob 44 and wire 24, thus loading the spring 50. The clamping knob is then released and the spring force urges the clamping knob and wire forwards. In this embodiment the stroke is 0.3 mm.

The operation of the drive unit is under the control of a trigger button 52.

To use the device shown in FIGS. 2 to 8, the catheter 26 is normally introduced first. If it passes through an occlusion, the apparatus need not be used. However, if it cannot pass through the occlusion the wire is fed, inside the catheter, up to the occlusion. The apparatus shown in the drawings may have been located on the wire prior to it being moved within the catheter, or after this. Once the wire is clamped the apparatus may be used to reciprocate the wire, and thereby help it to pass through the occlusion. Once it has passed through the occlusion the catheter should be able to advance, so that the balloon portion is located in place, to expand.

The wire 24 in the second embodiment is a "floppy" low-friction hydrophilic coated wire of 0.25 mm diameter and has a floppy coiled distal end region 5 cm in length. The distal end region bows under its own weight when projected about 5 cm beyond the end of the catheter. The distal tip is of simple rounded-off (non-bulbous) form.

In a third embodiment (not shown) the apparatus is again pistol-shaped but the catheter is not secured to the barrel by means of a spring-loaded clamp 38. Rather, the catheter hub is held by a "twist-lock" or bayonet-type fitting. Furthermore, there is no reciprocation adjustment in this embodiment, and so no reciprocation control knob 46 or reciprocation control spring 50 is required. The stroke is fixed at 0.2 mm. The wire is held in a quick release vice grip. The barrel 22 is removable from the butt portion, by unscrewing it. A plurality of barrels is provided, able to secure different types and sizes of catheter.

The reader's attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings), may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

I claim:

1. An apparatus for use in clearing a blockage in a body passage comprising:

a housing;

a catheter having a distal end with an opening having an axis;

a wire having a proximal end portion and a distal end portion, the wire adapted to guide the catheter, the distal end portion of the wire adopted to bow downwardly from horizontal when extended a distance equal to or less than five centimeters beyond the distal end of the catheter when in use;

means for moving the distal end portion of the wire extending beyond the distal end of the catheter diffusely in at least two degrees of freedom with respect to the axis of said opening, the means for moving including a drive unit mounted in the housing coupled to the proximal end portion of the wire to vibrate the distal end portion of the wire and;

means for clamping the catheter to the housing.

2. The apparatus as claimed in claim 1, wherein the catheter comprises an expandable balloon at a distal end of the catheter.

3. The apparatus as claimed in claim 1, wherein at least the distal end portion of the wire comprises a floppy portion.

4. The apparatus as claimed in claim 1, wherein the wire comprises a predetermined diameter in a range between 0.1 mm and 1 mm.

5. The apparatus as claimed in claim 1, wherein the distal end portion of the wire has an end region of a coiled construction.

6. The apparatus as claimed in claim 1, wherein the wire is a low-friction wire.

7. The apparatus as claimed in claim 1, wherein the catheter comprises a bore having a predetermined diameter greater than a predetermined diameter of the wire in a range between 10% and 50%.

8. The apparatus as claimed in claim 1, comprising a pistol-shaped housing for the drive unit.

9. The apparatus of claim 1, wherein the opening of the catheter has a diameter in the range of 10% to 90% greater than a diameter of the distal end portion of the wire to permit the diffuse movement.

* * * * *